United States Patent [19]

Crossley et al.

[11] 4,386,080
[45] May 31, 1983

[54] ANTI-ANDROGENIC AMIDE DERIVATIVE

[75] Inventors: Neville S. Crossley, Knutsford; Alasdair T. Glen; Leslie R. Hughes, both of Macclesfield, all of England

[73] Assignee: Imperial Chemical Industries Limited, London, England

[21] Appl. No.: 266,047

[22] Filed: May 21, 1981

[30] Foreign Application Priority Data

May 22, 1980 [GB] United Kingdom ............... 8016915

[51] Int. Cl.³ ............... C07C 103/22; C07C 103/26
[52] U.S. Cl. ............... 424/209; 260/465 D; 424/227; 424/240; 424/243; 424/271; 424/304; 424/309; 424/311; 424/272; 424/317; 424/324; 548/224; 560/250; 562/430; 562/432; 562/437; 562/458; 564/154; 564/155; 564/156; 564/158; 564/162; 564/166; 564/170; 564/172; 564/173; 564/180
[58] Field of Search ............... 564/154, 155, 156, 158, 564/172, 173, 180, 162, 166, 170, 182; 260/465 D; 560/250; 562/430, 432, 437, 458; 424/304, 309, 311, 317, 324, 272, 209, 227, 240, 243, 271; 548/224

[56] References Cited

U.S. PATENT DOCUMENTS

| | | | |
|---|---|---|---|
| 1,878,543 | 9/1932 | Rinele et al. ............... | 564/182 X |
| 2,721,216 | 10/1955 | Speeter ............... | 564/170 |
| 3,255,231 | 6/1966 | Green et al. ............... | 564/170 X |
| 3,282,939 | 11/1966 | Spivack et al. ............... | 564/170 X |
| 3,419,563 | 12/1968 | Knupfer et al. ............... | 564/182 X |
| 3,632,829 | 1/1972 | Schumecher et al. ............... | 564/170 X |
| 3,706,796 | 12/1972 | Blake ............... | 564/182 X |
| 4,049,713 | 9/1977 | Spivack et al. ............... | 564/170 X |
| 4,191,775 | 3/1980 | Glen ............... | 564/170 X |

FOREIGN PATENT DOCUMENTS

| | | | |
|---|---|---|---|
| 1160431 | 1/1964 | Fed. Rep. of Germany ...... | 564/182 |
| 40-4921 | 3/1965 | Japan ............... | 564/170 |
| 49-135048 | 4/1974 | Japan ............... | 564/182 |
| 345016 | 4/1960 | Switzerland ............... | 564/182 |
| 828695 | 2/1960 | United Kingdom ............... | 564/166 |

Primary Examiner—Thomas A. Waltz
Attorney, Agent, or Firm—Cushman, Darby & Cushman

[57] ABSTRACT

Novel 3,4-disubstituted-N-acylanilines of the formula:

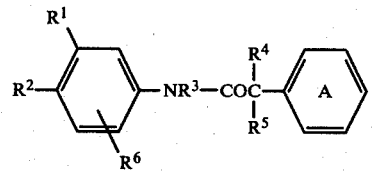

wherein $R^1$, $R^2$ and ring A are defined in claim 1;
wherein $R^3$ is hydrogen or alkyl of up to 4 carbon atoms, or is joined to $R^5$ as stated below;
wherein $R^4$ is alkyl of 2 to 4 carbon atoms, or has the formula $—CX^1X^2X^3$ wherein $X^1$, $X^2$ and $X^3$, which may be the same or different, each is hydrogen, fluorine or chlorine; wherein $R^5$ is hydrogen, hydroxy or alkoxy or acyloxy each of up to 15 carbon atoms, or is joined to $R^3$ to form an oxycarbonyl group such that together with the

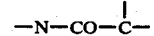

part of the molecule it forms an oxazolidinedione group; and wherein $R^6$ is hydrogen or halogen. These compounds possess antiandrogenic activity and are useful for the treatment of androgen dependent or prostatic diseases. Representative of the compounds is 3,4-dichloro-N-(2-hydroxy-2-p-nitrophenylpropionyl)aniline. Also disclosed are processes for the manufacture of the compounds and pharmaceutical and veterinary compositions containing them.

9 Claims, No Drawings

ANTI-ANDROGENIC AMIDE DERIVATIVE

This invention relates to new amide derivatives and more particularly it relates to novel acylanilides which possess antiandrogenic properties.

According to the invention there is provided an acylanilide of the formula:

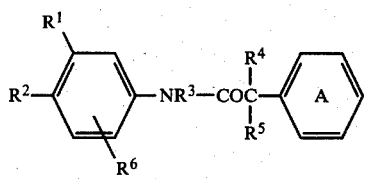

wherein $R^1$ is cyano, carbamoyl, nitro, fluoro, chloro, bromo, iodo or hydrogen; or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl; wherein $R^2$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl; wherein $R^3$ is hydrogen or alkyl of up to 4 carbon atoms, or is joined to $R^5$ as stated below; wherein $R^4$ is alkyl of 2 to 4 carbon atoms, or has the formula $-CX^1X^2X^3$ wherein $X^1$, $X^2$ and $X^3$, which may be the same or different, each is hydrogen, fluorine or chlorine; wherein $R^5$ is hydrogen, hydroxy or alkoxy or acyloxy each of up to 15 carbon atoms, or is joined to $R^3$ to form an oxycarbonyl group such that together with the

part of the molecule it forms an oxazolidinedione group; wherein $R^6$ is hydrogen or halogen; and wherein the benzene ring A bears one, two or three substituents selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or bears a buta-1,3-dienylene substituent which together with the benzene ring A forms a naphthalene ring.

It will be observed that the acylanilide derivative of the invention possesses an asymmetric carbon atom, namely the carbon atom which bears the substituents $R^4$ and $R^5$, and it can therefore exist in racemic and optically-active forms. It is to be understood that this invention encompasses the racemic form of the acylanilide derivative and any optically-active form which possesses antiandrogenic activity, it being a matter of common general knowledge how a racemic compound may be resolved into its optically-active forms and how any antiandrogenic activity present in any of these forms may be determined.

A suitable value for $R^1$, $R^3$ or a substituent in ring A when it is alkyl is, for example, methyl or ethyl. $R^3$ is preferably hydrogen.

A suitable value for $R^1$ or a substituent in ring A when it is alkoxy is, for example, methoxy or ethoxy.

A suitable value for $R^1$, $R^2$ or a substituent in ring A when it is alkanoyl is, for example, formyl or acetyl.

A suitable value for $R^1$, $R^2$ or a substituent in ring A when it is alkylthio, alkylsulphinyl, alkylsulphonyl, perfluoroalkyl, perfluoroalkylthio, perfluoroalkylsulphinyl or perfluoroalkylsulphonyl is, for example, methylthio, ethylthio, methylsulphinyl, methylsulphonyl, trifluoromethyl, pentafluoroethyl, trifluoromethylthio, trifluoromethylsulphinyl or trifluoromethylsulphonyl.

A suitable value for $R^4$ is, for example, methyl, ethyl, n-propyl, fluoromethyl, difluoromethyl, trifluoromethyl, chloromethyl, dichloromethyl or trichloromethyl. $R^4$ is preferably methyl.

A suitable value for $R^5$ when it is alkoxy is, for example, methoxy, ethoxy, propyloxy, n-butyloxy or decyloxy.

A suitable value for $R^5$ when it is acyloxy is, for example, alkanoyl or aroyl each of up to 15 carbon atoms, for example acetoxy, propionyloxy, decanoyloxy, dodecanoyloxy or benzoyloxy. $R^5$ is preferably hydroxy.

A suitable value for $R^6$ or a substituent in ring A when it is halogen is fluoro, chloro, bromo or iodo. $R^6$ is preferably hydrogen or chloro, especially hydrogen.

A suitable value for a substituent in ring A when it is alkoxycarbonyl or N-alkylcarbamoyl is, for example, methoxycarbonyl, ethoxycarbonyl or N-methylcarbamoyl.

A preferred combination of values for $R^1$ and $R^2$ is as follows:

| $R^1$ | $R^2$ |
|---|---|
| trifluoromethyl | nitro |
| trifluoromethyl | cyano |
| chloro | chloro |
| chloro | nitro |
| chloro | cyano |
| cyano | chloro |
| nitro | chloro |
| nitro | cyano |
| chloro | methylthio |
| chloro | methylsulphinyl |
| chloro | methylsulphonyl |
| methylthio | cyano |
| hydrogen | methylthio |

Ring A preferably contains one or two substituents only, one of which is an electron-withdrawing substituent in the para-position thereof, for example a nitro, fluoro, chloro, trifluoromethyl, cyano, methoxycarbonyl, methylthio, methylsulphinyl or methylsulphonyl substituent; and the other of which is hydrogen or chloro in the meta-position.

In particular, ring A preferably bears a single nitro substituent in the para-position.

A preferred acylanilide of the invention has the formula stated above wherein $R^1$ and $R^2$, which may be the same or different, each is cyano, nitro, trifluoromethyl or chloro, $R^3$ and $R^6$ are both hydrogen, $R^4$ is methyl, $R^5$ is hydroxy and the ring A bears one substituent in the para position which is a nitro, fluoro, trifluoromethyl, cyano, methoxycarbonyl, methylthio or methylsulphinyl substituent.

Specific acylanilides of the invention are hereinafter described in the Examples.

Particularly active compounds are 3,4-dichloro-N-(2-hydroxy-2-p-nitrophenylpropionyl) aniline;
4-nitro-3-trifluoromethyl-N-(2-hydroxy-2-p-nitrophenylpropionyl)aniline;
4-cyano-3-trifluoromethyl-N-(2-hydroxy-2-p-nitrophenylpropionyl)aniline;
3-chloro-4-nitro-N-(2-hydroxy-2-p-nitrophenylpropionyl)aniline;
3-chloro-4-methylsulphonyl-N-(2-hydroxy-2-p-nitrophenylpropionyl)aniline;
4-nitro-3-trifluoromethyl-N-(2-hydroxy-2-p-trifluoromethylphenylpropionyl)aniline;
3-chloro-4-nitro-N-(2-hydroxy-2-p-trifluoromethylphenylpropionyl)aniline;
4-nitro-3-trifluoromethyl-N-(2-p-cyanophenyl-2-hydroxypropionyl)aniline;
4-nitro-3-trifluoromethyl-N-(2-p-fluorophenyl-2-hydroxypropionyl)aniline;
4-nitro-3-trifluoromethyl-N-(2-hydroxy-2-p-methylsulphinylphenylpropionyl)aniline;
3,4-dichloro-N-(2-hydroxy-2-p-methylsulphinylphenylpropionyl)aniline; and
3,4-dichloro-N-(2-p-acetylphenyl-2-hydroxypropionyl)aniline.

The acylanilides of the invention may be manufactured by any chemical process known to be suitable for the manufacture of chemically-analogous compounds.

A preferred process for the manufacture of an acylanilide of the invention wherein $R^3$ is hydrogen and $R^5$ is other than hydroxy comprises the reaction of an amine of the formula:

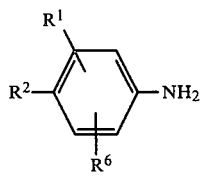

wherein $R^1$, $R^2$ and $R^6$ have the meanings stated above, with an acid of the formula:

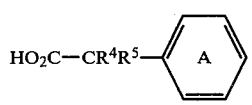

wherein $R^4$ and A have the meanings stated above and wherein $R^5$ is hydrogen, alkoxy or acyloxy, or with a reactive derivative of said acid.

A suitable reactive derivative of an acid is, for example, an acid anhydride, or an acyl halide, for example an acyl chloride, or a lower alkyl ester of said acid, for example the methyl or ethyl ester. Preferably the reaction is carried out in pyridine solution using an acyl chloride (prepared from the acid and thionyl chloride) as reactant.

The abovementioned process is especially valuable for the manufacture of an acylanilide derivative of the invention wherein $R^5$ is acyloxy.

An acylanilide of the invention wherein $R^3$ and $R^5$ are joined together to form a carbonyl-oxy group that is, an oxazolidinedione, may be prepared by the reaction of an isocyanate of the formula:

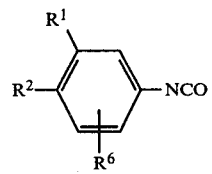

wherein $R^1$, $R^2$ and $R^6$ have the meanings stated above, with an ester of the formula:

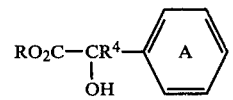

wherein $R^4$ and A have the meanings stated above and wherein R is alkyl of up to 6 carbon atoms, for example methyl or ethyl. This reaction is preferably carried out in an organic solvent, for example diethyl ether, at laboratory temperature.

An acylanilide of the invention wherein $R^5$ is hydroxy may be prepared by the hydrolysis of the corresponding acylanilide wherein $R^5$ is acyloxy, and this is a particularly important method for preparing such compounds when the acylanilide wherein $R^5$ is acyloxy has been prepared by the preferred process of the invention. An acylanilide of the invention wherein $R^5$ is hydroxy and $R^3$ is hydrogen may be prepared by the hydrolysis of the corresponding oxazolidinedione, which may be prepared as described in the preceding paragraph.

An acylanilide of the invention wherein $R^3$ is alkyl may be prepared by the alkylation of the corresponding acylanilide wherein $R^3$ is hydrogen.

An acylanilide of the invention wherein $R^5$ is acyloxy may be prepared by the acylation of the corresponding acylanilide wherein $R^5$ is hydroxy.

An oxazolidinedione of the invention, wherein $R^3$ and $R^5$ are joined together to form a carbonyl-oxy group, may be prepared by the reaction of the corresponding acylanilide wherein $R^3$ is hydrogen and $R^5$ is hydroxy with phosgene ($COCl_2$).

An acylanilide of the invention wherein $R^4$ is chloromethyl and $R^5$ is hydroxy may be prepared by the reaction of an epoxide of the formula

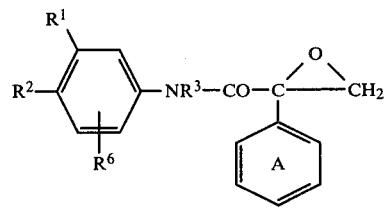

wherein $R^1$, $R^2$, $R^3$, $R^6$ and A have the meanings stated above, with hydrogen chloride. This reaction is preferably carried out in an organic solvent, for example chloroform, at laboratory temperature.

The starting material for the last-mentioned reaction may be prepared by the reaction of an aniline of the formula

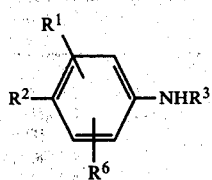

wherein $R^1$, $R^2$, $R^3$ and $R^6$ have the meanings stated above, with an epoxide of the formula:

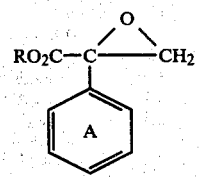

wherein R and A have the meanings stated above.

An acylanilide of the invention wherein one or more of $R^1$, $R^2$ and a substituent in the benzene ring A is alkylsulphinyl, perfluoroalkylsulphinyl or phenylsulphinyl, or is alkylsulphonyl, perfluoroalkylsulphonyl or phenylsulphonyl, may be prepared by the oxidation of the corresponding acylanilide wherein one or more of $R^1$, $R^2$ and a substituent in the benzene ring A is alkylthio, perfluoroalkylthio or phenylthio, respectively. The oxidising agent and conditions used will determine whether a sulphinyl or a sulphonyl compound is obtained. Thus, oxidation with sodium metaperiodate in methanol solution at or below laboratory temperature will generally convert a thio compound into the corresponding sulphinyl compound; and oxidation with hydrogen peroxide in acetic acid solution at or above laboratory temperature will generally convert a thio compound into the corresponding sulphonyl compound.

An acylanilide of the invention wherein the benzene ring A bears a carboxy substituent may be prepared by the oxidation of the corresponding acylanilide wherein the benzene ring A bears a formyl substituent; and an acylanilide of the invention wherein the benzene ring A bears an alkoxycarbonyl substituent may be prepared by the esterification of the corresponding acylanilide wherein the benzene ring a bears a carboxy substituent.

As stated above, an acylanilide of the invention possesses antiandrogenic properties as demonstrated by its ability to decrease the weight of the seminal vesicles of a mature male rat when administered orally for 4 successive days. An acylanilide of the invention may therefore be used in the treatment of, for example, malignant or benign prostatic disease or of androgen-dependent disease conditions, such as acne, hirsutism or seborrhoea, in warm-blooded vertebrates including man. It may also be used to improve ovulation in a domestic animal.

A preferred acylanilide of the invention is up to 25 times more active as an antiandrogen than the known, chemically-related antiandrogens flutamide and hydroxyflutamide. At a dose of an acylanilide of the invention which produces antiandrogenic activity in rats no symptoms of toxicity are apparent.

The acylanilide of the invention may be administered to a warm-blooded animal in the form of a pharmaceutical of veterinary composition which comprises the acylanilide in association with a pharmaceutically-acceptable diluent or carrier.

The composition may be in a form suitable for oral dosage, as a tablet, capsule, aqueous or oily solution or suspension or emulsion. It may alternatively be in the form of a sterile solution or suspension suitable for parenteral administration, or be in the form of an ointment or lotion for topical administration, or be in the form of a suppository.

The composition may additionally contain one or more drugs selected from anti-oestrogens, for example tamoxifen; progestins, for example medroxyprogesterone acetate; inhibitors of gonadotrophin secretion, for example danazol; cytotoxic agents, for example cyclophosphamide; antibiotics, for example penicillin or oxytetracyclin; and anti-inflammatory agents, for example, especially for topical use, fluocinolone acetonide.

The acylanilide of the invention will normally be administered to a warm-blooded animal at a dose of between 0.1 mg. and 125 mg. per kg. bodyweight.

The invention is illustrated but not limited by the following Examples:

EXAMPLE 1

Pyridine (0.46 ml.) and thionyl chloride (0.34 ml) were added to a solution of 2-acetoxy-2-p-nitrophenylpropionic acid (1.23 g.) in methylene chloride (20 ml.) and the mixture was stirred at laboratory temperature for 30 minutes and then evaporated to dryness under reduced pressure. The residue was dissolved in pyridine (25 ml.), 3,4-dichloroaniline (0.78 g.) was added and the mixture was stirred for 17 hours and then evaporated to dryness. The residue was partitioned between ethyl acetate and dilute aqueous hydrochloric acid, and the ethyl acetate solution was separated, washed successively with dilute aqueous hydrochloric acid, water, aqueous sodium bicarbonate solution and saturated aqueous sodium chloride solution, then dried over magnesium sulphate and evaporated to dryness under reduced pressure. The residue was crystallised from toluene and there was thus obtained 3,4-dichloro-N-(2-acetoxy-2-p-nitrophenylpropionyl)aniline, m.p. 135°–136° C.

This product (1.0 g.) was dissolved in a 20:1 v/v mixture of ethanol and tetrahydrofuran (25 ml.), 5% aqueous potassium hydroxide solution (5 ml.) was added and the mixture was allowed to stand for 10 minutes and was then evaporated to dryness. The residue was partitioned between ethyl acetate and saturated aqueous medium sodium chloride solution, and the ethyl acetate solution was separated, dried over magnesium sulphate and evaporated to dryness. The residue was crystallised from toluene and there was thus obtained 3,4-dichloro-N-(2-hydroxy-2-p-nitrophenylpropionyl)aniline, m.p. 179°–180° C.

The 2-acetoxy-2-p-nitrophenylpropionic acid used as starting material was obtained as follows:

Zinc iodide (0.05 g.) and trimethylsilyl cyanide (36 g.) were added to a stirred solution of p-nitroacetophenone (50 g.) in methylene dichloride (500 ml.) and the mixture was stirred at laboratory temperature for 48 hours and then evaporated to dryness under reduced pressure. Aqueous 3 N-hydrochloric acid (500 ml.) was added and the mixture was heated at 50° C. for 5 hours, cooled and poured into water. The mixture was extracted three times with ethyl acetate and the combined extracts were washed with water and then with saturated aqueous sodium chloride solution, dried over magnesium sulphate and evaporated to dryness under reduced pressure. A mixture of the 2-hydroxy-2-p-nitrophenylpropiononitrile thus obtained (1.2 g.) and concentrated aqueous hydrochloric acid (20 ml.) was heated for 4 hours at 110° C. in a sealed tube. The mixture was diluted with water and extracted with ethyl acetate, and the ethyl acetate extract was washed successively with water and saturated aqueous sodium chloride solution, dried over magnesium sulphate and evaporated to dryness under reduced pressure. A mixture of the 2-hydroxy-2-p-nitrophenylpropionic acid thus obtained (1.3 g.), acetic anhydride (1.25 ml.) and pyridine (20 ml.) was stirred at laboratory temperature for 17 hours and then evaporated to dryness under reduced pressure. The residue was partitioned between ethyl acetate and dilute aqueous hydrochloric acid and the ethyl acetate solution was separated, washed successively with dilute aqueous hydrochloric acid, water and saturated aqueous sodium chloride solution, dried over magnesium sulphate and evaporated to dryness under reduced pressure. There was thus obtained as solid residue 2-acetoxy-2-p-nitrophenylpropionic acid which was used without further purification.

EXAMPLE 2

The process described in the first and second paragraph of Example 1 was repeated except that the appropriate aniline and the appropriate 2-acetoxy-2-phenylalkanoic acid were used as starting materials. There were thus obtained the compounds described in the following table:

| $R^1$ | $R^2$ | $R^4$ | Ring A Substituent | m.p. (°C.) |
|---|---|---|---|---|
| Cl | Cl | $CH_3$ | — | 127–128 |
| Cl | Cl | $CH_3$ | 3-$NO_2$ | 150–151 |
| Cl | Cl | $CH_3$ | 3-$NO_2$—4-Cl | 120–122 |
| Cl | Cl | $CH_3$ | 3-$CF_3$ | 118–119 |
| Cl | Cl | $CH_3$ | 4-Cl | 143–145 |
| Cl | Cl | $CF_3$ | — | 118–119 |
| Cl | Cl | $CF_3$ | 3-$CH_3O$ | (gum) |
| $CF_3$ | $NO_2$ | $CH_3$ | — | 116–117 |
| $CF_3$ | $NO_2$ | $CH_3$ | 4-$NO_2$ | 126–127 |
| $CF_3$ | $NO_2$ | $CH_3$ | 3-$NO_2$ | 175–176 |
| $CF_3$ | $NO_2$ | $CH_3$ | 3-$NO_2$—4-Cl | 122–123 |
| $CF_3$ | $NO_2$ | $CH_3$ | 2-$NO_2$ | 180–181 |
| $CF_3$ | $NO_2$ | $CH_3$ | 4-$CF_3$ | 137–143 |
| $CF_3$ | $NO_2$ | $CH_3$ | 3-$CF_3$ | 120–121 |
| $CF_3$ | $NO_2$ | $CH_3$ | 4-Cl | 108–109 |
| $CF_3$ | $NO_2$ | $CH_3$ | 3-Cl | 133–134 |
| $CF_3$ | $NO_2$ | $CH_3$ | 3,4-diCl | 146–147 |
| $CF_3$ | $NO_2$ | $CF_3$ | — | 134–136 |
| $CF_3$ | $NO_2$ | $CF_3$ | 4-Cl | 131–132 |
| $CF_3$ | $NO_2$ | $CF_3$ | 4-$CH_3$ | 147–148 |
| $CF_3$ | CN | $CH_3$ | 4-$NO_2$ | 186–188 |
| $CH_3O$ | CN | $CH_3$ | 4-$NO_2$ | 155–156 |
| $NO_2$ | Cl | $CH_3$ | 4-$NO_2$ | 160–162 |

EXAMPLE 3

The process described in the first and second paragraphs of Example 1 was repeated except that the appropriate aniline and the appropropriate 2-acetoxy-2-phenylalkanoic acid were used as starting materials. There were thus obtained the compounds described in the following table:

| $R^1$ | $R^2$ | $R^4$ | Ring A Substituent | m.p. (°C.) |
|---|---|---|---|---|
| Cl | Cl | $CH_3$ | 4-$CF_3$ | 130–131 |
| Cl | Cl | $CH_3$ | 4-F | 131–132 |
| Cl | Cl | $CH_3$ | 4-CN | 159–161 |
| Cl | Cl | $CH_3$ | 4-$C_6H_5$ | 135–136 |
| Cl | Cl | $CH_3$ | 4-CHO | 137–138 |
| Cl | Cl | $CH_3$ | 4-$COCH_3$ | (gum) |
| Cl | Cl | $CH_3$ | 4-$SC_6H_5$ | (gum) |
| Cl | Cl | $CH_3$ | 4-$SCH_3$ | 154–157 |
| $CF_3$ | $NO_2$ | $CH_3$ | 4-$NO_2$ | 128–130 (−)-isomer |
| $CF_3$ | $NO_2$ | $CH_3$ | 4-$NO_2$ | 139–140 (+)-isomer |
| $CF_3$ | $NO_2$ | $CH_3$ | 4-F | 107–108 |
| $CF_3$ | $NO_2$ | $CH_3$ | 4-CN | 125–130 |
| $CF_3$ | $NO_2$ | $CH_3$ | 4-$C_6H_5$ | 168–169 |
| $CF_3$ | $NO_2$ | $CH_3$ | (1-naphthyl) | 182–185 |
| $CF_3$ | $NO_2$ | $CH_3$ | (2-naphthyl) | 111–113 |
| $CF_3$ | $NO_2$ | $CH_3$ | 4-CHO | 55–57 |
| $CF_3$ | $NO_2$ | $CH_3$ | 4-$COCH_3$ | 133–134 |
| $CF_3$ | $NO_2$ | $CH_3$ | 4-$SCH_3$ | 118–122 |
| $CF_3$ | $NO_2$ | $CH_3$ | 4-$SC_6H_5$ | (gum) |
| $CF_3$ | CN | $CH_3$ | 4-$CF_3$ | 191–192 |
| $CF_3$ | F | $CH_3$ | 4-$NO_2$ | 120–122 |
| $CF_3$ | Br | $CH_3$ | 4-$NO_2$ | 139–140 |
| Cl | $COCH_3$ | $CH_3$ | 4-$NO_2$ | 136–139 |
| Cl | $CH_3S$ | $CH_3$ | 4-$NO_2$ | 153–154 |
| Cl | $CH_3S$ | $CH_3$ | 4-$CF_3$ | (gum) |
| Cl | $CH_3S$ | $CH_3$ | 4-CN | (gum) |
| Cl | $NO_2$ | $CH_3$ | 4-$NO_2$ | 179–180 |
| Cl | $NO_2$ | $CH_3$ | 4-$CF_3$ | 161–162 |
| Cl | $NO_2$ | $CH_3$ | 4-F | 123–124 |
| Cl | $NO_2$ | $CH_3$ | 4-CN | 152–154 |
| Cl | $NO_2$ | $CH_3$ | 4-$COCH_3$ | 58 |
| Cl | $NO_2$ | $CH_3$ | 4-$SCH_3$ | (gum) |
| Cl | CN | $CH_3$ | 4-$NO_2$ | 189–190 |
| Cl | CN | $CH_3$ | 4-$CF_3$ | 202–203 |
| Cl | CN | $CH_3$ | 4-F | 132–133 |
| Cl | CN | $CH_3$ | 4-CN | 96–98 |
| Cl | CN | $CH_3$ | 4-CHO | 79–81 |
| Cl | CN | $CH_3$ | 4-$COCH_3$ | 64–67 |
| Cl | CN | $CH_3$ | 4-$SCH_3$ | (gum) |
| Cl | CN | $CH_3$ | 4-$SC_6H_5$ | (gum) |
| CN | Cl | $CH_3$ | 4-$NO_2$ | 156–157 |
| $NO_2$ | Cl | $CH_3$ | 4-$CF_3$ | 118–120 |
| $NO_2$ | CN | $CH_3$ | 4-$NO_2$ | 92–93 |
| $NO_2$ | CN | $CH_3$ | 4-$SCH_3$ | (gum) |
| $NO_2$ | CN | $CH_3$ | 4-$CF_3$ | 167–169 |
| $NO_2$ | CN | $CH_3$ | 4-CN | 115–118 |
| $CH_3S$ | CN | $CH_3$ | 4-$NO_2$ | 148–149 |
| $CH_3S$ | CN | $CH_3$ | 4-$CF_3$ | (gum) |
| $CH_3S$ | CN | $CH_3$ | 4-$SCH_3$ | (gum) |
| $CH_3$ | CN | $CH_3$ | 4-$NO_2$ | 171–172 |
| $CH_3O$ | CN | $CH_3$ | 4-$CF_3$ | 165–167 |
| $NO_2$ | Cl | $CH_3$ | 4-CN | 129–134 |
| $H_2NCO$ | Cl | $CH_3$ | 4-$NO_2$ | 208–210 |
| H | $CF_3$ | $CH_3$ | 4-$NO_2$ | 153–154 |
| H | $CF_3S$ | $CH_3$ | 4-$NO_2$ | 164–165 |
| H | $CH_3S$ | $CH_3$ | 4-$NO_2$ | 161–162 |
| $C_6H_5S$ | $NO_2$ | $CH_3$ | 4-$NO_2$ | (gum) |
| $CF_3$ | $NO_2$ | $CF_3$ | 3-$CH_3$ | 165–166 |
| Cl | Cl | $CF_3$ | 4-Cl | 135 |
| $CF_3$ | $NO_2$ | $C_2H_5$ | — | 125–128 |
| $CF_3$ | $NO_2$ | n-$C_3H_7$ | — | 107–108 |
| Cl | Cl | n-$C_3H_7$ | — | 85–86 |
| Cl | Cl | $CHF_2$ | 4-$SCH_3$ | (gum) |
| Cl | Cl | $CHCL_2$ | 4-$SCH_3$ | (gum) |
| Cl | CN | $CHCl_2$ | 4-$SCH_3$ | (gum) |
| Cl | Cl | $CH_2F$ | — | 115–116 |

There were also similarly prepared 3,4,5-trichloro-N-(2-hydroxy-2-p-nitrophenylpropionyl)aniline, m.p. 232°–235° C. and 2-chloro-4-nitro-N-(2-hydroxy-2-p-nitrophenylpropionyl)aniline, m.p. 155°–157° C.

EXAMPLE 4

The process described in the first part of Example 1 was repeated except that 4-nitro-3-trifluoromethylaniline and the appropriate 2-acyloxy-2-p-nitrophenylpropionic acid were used as starting materials. There were thus obtained the compounds described in the following table:

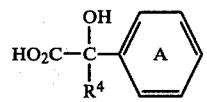

| R⁵ | m.p. (°C.) |
| --- | --- |
| acetoxy | 163–164 |
| benzoyloxy | 98–100 |
| n-dodecanoyloxy | 50–70 |

PREPARATION OF STARTING MATERIALS

The 2-acyloxy-2-phenylalkanoic acids used as starting materials in Examples 2, 3 and 4 were obtained from the corresponding 2-hydroxy-2-phenylalkanoic acids by a similar process to that described in the final part of Example 1. The 2-hydroxy-2-phenylalkanoic acids themselves were obtained either (a) from the corresponding alkanophenone by a similar process to that described in the final part of Example 1, or (b) by the reaction of an aryl-metallo compound with an α-ketoacid as exemplified by the following preparation of 2-p-fluorophenyl-2-hydroxypropionic acid:

A Grignard reagent was prepared from a solution of 1-bromo-4-fluorobenzene (50 g.) in diethyl ether (100 ml.) and a stirred suspension of magnesium (6.8 g.) in diethyl ether (20 ml.), and was heated under reflux for 1 hour and then cooled to 0° C. A solution of pyruvic acid (10.8 g.) in diethyl ether (50 ml.) was added dropwise and the mixture was stirred at laboratory temperature for 17 hours, cooled to 0° C., acidified with dilute aqueous hydrochloric acid and extracted three times with diethyl ether. The combined ethereal extracts were washed with water and extracted with saturated aqueous sodium bicarbonate solution, and the bicarbonate extract was acidified with concentrated aqueous hydrochloric acid and then extracted three times with ethyl acetate. The combined ethyl acetate extracts were washed with water and then with saturated aqueous sodium chloride solution, dried over magnesium sulphate and evaporated to dryness under reduced pressure. There was thus obtained as residue 2-p-fluorophenyl-2-hydroxypropionic acid which was used without further purification.

Process (b) described above was used to prepare 2-aryl-2-hydroxypropionic acids wherein the 2-aryl group was:

| | |
| --- | --- |
| 3-chlorophenyl | 4-methylthiophenyl |
| 4-chlorophenyl | 4-phenylthiophenyl |
| 3-trifluoromethylphenyl | 1-naphthyl |
| 4-trifluoromethylphenyl | 2-naphthyl |

Process (b) described above was also used to prepare 2-p-diethoxymethylphenyl- and 2-p-(1,1-diethoxyethyl)phenyl-2-hydroxypropionic acid, which were hydrolysed to 2-p-formylphenyl- and 2-p-acetylphenyl-2-hydroxypropionic acid respectively by heating under reflux for 17 hours in dioxan solution with aqueous 2 N-sulphuric acid.

2-p-Cyanophenyl-2-hydroxypropionic acid was prepared by a similar process to process (b) except that the organolithium compound prepared from a solution of 4-bromobenzonitrile (2 g.) in tetrahydrofuran (100 ml.) and n-butyl-lithium (7.3 ml of a 1.5 molar solution in hexane) at −90° C. was added to a solution of ethyl pyruvate (1.2 ml.) in tetrahydrofuran (100 ml.) at −100° C., the reaction mixture was worked up in conventional manner, and the ethyl ester was hydrolysed to the acid by conventional means.

Process (a) described above was used to prepare the following acids of the formula:

$$HO_2C-\underset{R^4}{\underset{|}{\overset{OH}{\overset{|}{C}}}}-\!\!\left\langle\!\!\!\begin{array}{c}A\end{array}\!\!\!\right\rangle$$

| R⁴ | Ring A Substituent | R⁴ | Ring A Substituent |
| --- | --- | --- | --- |
| CH₃ | 2-NO₂ | CF₃ | 4-Cl |
| CH₃ | 3-NO₂ | CF₃ | 3-CH₃O |
| CH₃ | 3,4-diCl | CF₃ | 4-CH₃ |
| CH₃ | 3-NO₂—4-Cl | CF₃ | 3-CH₃ |
| CHF₂ | 4-CH₃S | CF₃ | — |
| CHCl₂ | 4-CH₃S | CH₂F | — |

2-Hydroxy-2-phenylpropionic, butyric and valeric acids, and 2-hydroxy-2-(4-biphenylyl)propionic acid are known compounds.

All the alkanophenones used as starting materials in process (a) are known compounds apart from 4-methylthio-α,α-difluoroacetophenone which was prepared as follows:

n-Butyl-lithium (3.25 ml. of a 1.6 molar solution) was added dropwise to a stirred solution of 1-bromo-4-methylthiobenzene (1.06 g.) in tetrahydrofuran (50 ml.) which was maintained at −78° C., and the mixture was stirred at that temperature for 1 hour and then added to a solution of difluoroacetic acid (0.25 g.) in tetrahydrofuran (30 ml.). The mixture was stirred at −78° C. for 2 hours, acetic acid (0.5 ml.) was added and the mixture was allowed to warm up to room temperature and was then poured into water. The organic layer was separated, washed successively with saturated aqueous sodium bicarbonate solution, water and saturated sodium chloride solution, dried over magnesium sulphate and evaporated to dryness under reduced pressure. The residue consisted of 4-methylthio-α,α-difluoroacetophenone and was used without further purification.

All the anilines used as starting materials in Examples 2, 3 and 4 are known compounds apart from 4-cyano-3-methylthioaniline, which was prepared as follows:

A stirred mixture of 2-chloro-4-nitrobenzoic acid (12.1 g.), dimethyldisulphide (2.8 ml.), copper powder (3.8 g.) and N,N-dimethylacetamide (80 ml.) was heated to 135° C. during 1 hour, kept at that temperature for 90 minutes, and then heated at 165° C. for 2 hours. The N,N-dimethylacetamide was removed by distillation under reduced pressure and the residue was poured into a mixture of water (400 ml.) and 32% w/v aqueous sodium hydroxide solution (10 ml.). The mixture was filtered and the filtrate was washed with ethyl acetate, acidified with concentrated aqueous hydrochloric acid and filtered. The solid residue was washed with water and then dissolved in ethyl acetate, and the solution was dried over magnesium sulphate and evaporated to dryness under reduced pressure. The residue was crystallised from aqueous ethanol and there was thus obtained 2-methylthio-4-nitrobenzoic acid, m.p. 214°-215° C.

Thionyl chloride (29 ml.) was added to a stirred suspension of the above compound (42.6 g.) in petroleum ether, b.p. 60°-80° C. (800 ml.) containing piperidine (0.1 ml.) and the mixture was heated under reflux for 150 minutes and then evaporated to dryness under reduced pressure. A solution of the residue in tetrahydrofuran (100 ml.) was added to a stirred mixture of aqueous ammonium hydroxide solution (190 ml., specific gravity 0.88) and ice (250 g.) and the mixture was stirred at laboratory temperature for 16 hours, acidified with concentrated aqueous hydrochloric acid and filtered. The solid residue was washed with ice-cold water, and then stirred with saturated aqueous sodium bicarbonate solution, and the mixture was filtered. There was thus obtained as solid residue 2-methylthio-4-nitrobenzamide, m.p. 202°-204° C.

Trifluoroacetic anhydride (25.8 ml.) was added to a cooled, stirred suspension of the above compound (35.25 g.) in a mixture of dioxane (400 ml.) and pyridine (28 ml.) at such a rate that the temperature of the mixture was maintained at 10°-12° C., and the mixture was then stirred at laboratory temperature for 15 hours and poured into ice-water (3 liters). The mixture was filtered and the solid residue was crystallised from ethanol. There was thus obtained 2-methylthio-4-nitrobenzonitrile, m.p. 180°-181° C.

The above compound (30 g.) was added in portions during 50 minutes to a stirred mixture of water (800 ml.), ethanol (200 ml.), glacial acetic acid (60 ml.) and iron powder (150 g.) which was heated at 85°-90° C., and the mixture was stirred at this temperature for a further 3 hours and then basified to pH 9 with aqueous sodium hydroxide solution. The mixture was shaken with diethyl ether (200 ml.) and the whole mixture filtered through a filter-aid. The solid residue was washed with diethyl ether (400 ml) and the aqueous part of the filtrate was extracted five times with diethyl ether (100 ml. each time). The combined ethereal solutions were washed with saturated aqueous sodium chloride solution, dried over magnesium sulphate and evaporated to dryness. The residue consisted of 4-cyano-3-methylthioaniline, m.p. 105°-107.5° C.

EXAMPLE 5

A mixture of 2-methoxy-2-p-nitrophenylpropionic acid (0.3 g.) and thionyl chloride (3 ml.) was heated under reflux for 1 hour, evaporated to dryness under reduced pressure and the residue was dissolved in pyridine (15 ml.). 4-Nitro-3-trifluoromethylaniline (0.25 g.) was added and the mixture was stirred at laboratory temperature for 17 hours and then evaporated to dryness under reduced pressure. The residue was partitioned between ethyl acetate and dilute aqueous hydrochloric acid and the ethyl acetate layer was washed successively with water, saturated aqueous sodium bicarbonate solution and saturated aqueous sodium chloride solution, then dried over magnesium sulphate and evaporated to dryness under reduced pressure. The residue was purified by chromatography on a silica gel column (20 g.) using a 4.1 v/v mixture of toluene and ethyl acetate as eluant, and the product obtained was crystallised from toluene. There was thus obtained N-(2-methoxy-2-p-nitrophenylpropionyl)-4-nitro-3-trifluoromethylaniline, m.p. 151°-153° C.

The 2-methoxy-2-p-nitrophenylpropionic acid used as starting material was obtained as follows:

A mixture of 2-hydroxy-2-p-nitrophenylpropionic acid (0.7 g.; last paragraph of Example 1), concentrated sulphuric acid (0.5 ml.) and methanol (30 ml.) was heated under reflux for 3 hours, evaporated to dryness under reduced pressure and the residue was partitioned between ethyl acetate and water. The ethyl acetate layer was washed successively with saturated aqueous sodium bicarbonate solution, water and saturated aqueous sodium chloride solution, dried over magnesium sulphate and evaporated to dryness under reduced pressure. The residual methyl 2-hydroxy-2-p-nitrophenylpropionate (0.45 g.) was added to a stirred mixture of potassium hydroxide (0.45 g.) and dimethyl sulphoxide (2 ml.) which has been stirred for 5 minutes under an atmosphere of argon, methyl iodide (0.56 g.) was added immediately and the mixture was stirred for 2 hours at laboratory temperature under an atmosphere of argon. Water (5 ml.) was then added and the mixture was extracted with ethyl acetate. The extract was washed with water and then with saturated aqueous sodium chloride solution, dried over magnesium sulphate and evaporated to dryness under reduced pressure. A mixture of the residue, ethanol (5 ml.) and aqueous 2 N-sodium hydroxide solution (0.76 ml.) was heated under reflux for 1 hour, stirred at laboratory temperature for 17 hours and then evaporated to dryness under reduced pressure. The residue was partitioned between ethyl acetate and dilute aqueous hydrochloric acid. The ethyl acetate layer was washed with water, dried over magnesium sulphate and evaporated to dryness under reduced pressure. The residue consisted of 2-methyl-2-p-nitrophenylpropionic acid and was used without further purification.

The process described above was repeated using 2-n-butoxy-2-p-nitrophenylpropionic acid (prepared as described in the second paragraph above except that n-butyl iodide was used in place of methyl iodide) as starting material. There was thus obtained N-(2-n-butoxy-2-p-nitrophenylpropionyl)-4-nitro-3-trifluoromethylaniline, m.p. 124°-127° C.

EXAMPLE 6

A mixture of 2-p-nitrophenylpropionic acid (2.4 g.), methylene chloride (40 ml.), pyridine (0.98 ml.) and thionyl chloride (0.83 ml.) was stirred at laboratory temperature for 1 hour and then evaporated to dryness under reduced pressure. The residue was dissolved in pyridine (50 ml.), 4-nitro-3-trifluoromethylaniline (2.5 g.) was added and the mixture was stirred at laboratory temperature for 17 hours and then evaporated to dryness under reduced pressure. The residue was partitioned between ethyl acetate and dilute aqueous hydrochloric acid and the ethyl acetate layer was washed successively with dilute aqueous hydrochloric acid, water, saturated aqueous sodium bicarbonate solution and saturated aqueous sodium chloride solution, dried over magnesium sulphate and evaporated to dryness under reduced pressure. The residue was purified by chromatography on a silica gel column (120 g.) using a 3:2 v/v mixture of chloroform and ethyl acetate as eluant, and the product was crystallised from toluene. There was thus obtained 4-nitro-3-trifluoromethyl-N-(2-p-nitrophenylpropionyl)aniline, m.p. 161°-162° C.

The 2-p-nitrophenylpropionic acid used as starting material was obtained as follows:

Diethyl malonate (11 g.) was added dropwise to a stirred mixture of sodium hydride (3 g. of a 50% dispersion in mineral oil from which the oil has been removed by washing with petroleum ether) and dimethylformamide (150 ml.) and the mixture was stirred at laboratory temperature for 1 hour. A solution of 4-nitrochlorobenzene (10 g.) in dimethylformamide (15 ml.) was added dropwise, and the mixture was then heated at 100° C. for 17 hours, cooled and evaporated to dryness under reduced pressure. The residue was partitioned between ethyl acetate and water and the ethyl acetate layer was washed with water and then with saturated aqueous sodium chloride solution, dried over magnesium sulphate and evaporated to dryness under reduced pressure. The residue was distilled and there was thus obtained diethyl 2-methyl-p-nitrophenylmalonate, b.p. 143°–145° C./0.15 mm.Hg.

A mixture of the above compound (4.0 g.), aqueous 2 N-sodium hydroxide solution (20 ml.) and ethanol (100 ml.) was stirred at laboratory temperature for 17 hours and then evaporated to dryness under reduced pressure. To the residue were added water (80 ml.) and concentrated aqueous hydrochloric acid (20 ml.) and the mixture was heated at 100° C. for 6 hours, cooled and extracted 3 times with ethyl acetate. The combined extracts were themselves extracted 3 times with saturated aqueous bicarbonate solution and the combined extracts were acidified with concentrated aqueous hydrochloric acid and extracted three times with ethyl acetate. The combined extracts were washed with water and then with saturated aqueous sodium chloride solution, dried over magnesium sulphate and evaporated to dryness under reduced pressure. The residue consisted of 2-p-nitrophenylpropionic acid and was used without further purification.

EXAMPLE 7

A solution of sodium metaperiodate (0.79 g.) in water (14.7 ml.) was added dropwise to a stirred solution of 4-nitro-3-trifluoromethyl-N-(2-hydroxy-2-p-methylthiophenylpropionyl) aniline (Example 3; 1.4 g.) in methanol (35 ml.) which was maintained at 0° C. The mixture was allowed to warm up to laboratory temperature and was then stirred for 17 hours. Saturated aqueous sodium chloride solution (50 ml.) was added and the mixture was extracted twice with ethyl acetate (50 ml. each time). The combined extracts were washed with saturated aqueous sodium chloride solution, dried over magnesium sulphate and evaporated to dryness. The residue was crystallised from a mixture of ethyl acetate and petroleum ether (b.p. 60°–80° C.) and there was thus obtained 4-nitro-3-trifluoromethyl-N-(2-hydroxy-2-p-methanesulphinylphenylpropionyl)aniline, m.p. 171°–175° C.

The process described above was repeated using the appropriate anilide bearing an alkylthio or arylthio substituent and there were thus obtained the compounds described in the following table:

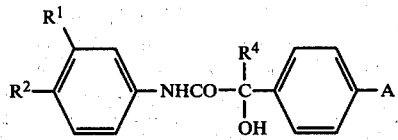

| $R^1$ | $R^2$ | $R^4$ | A | m.p. (°C.) |
|---|---|---|---|---|
| Cl | Cl | $CH_3$ | $SOCH_3$ | 170–181 |
| Cl | Cl | $CH_3$ | $SOC_6H_5$ | 179–181 |
| $CF_3$ | $NO_2$ | $CH_3$ | $SOC_6H_5$ | 156–158 |
| Cl | CN | $CH_3$ | $SOCH_3$ | 110–111 |
| Cl | CN | $CH_3$ | $SOC_6H_5$ | 195–197 |
| Cl | $NO_2$ | $CH_3$ | $SOCH_3$ | 179–180 |
| $NO_2$ | CN | $CH_3$ | $SOCH_3$ | 226–227 |
| Cl | $SOCH_3$ | $CH_3$ | $NO_2$ | 253–254 |
| Cl | $SOCH_3$ | $CH_3$ | CN | 148–155 |
| H | $SOCH_3$ | $CH_3$ | $NO_2$ | 138–139 |
| H | $SOCF_3$ | $CH_3$ | $NO_2$ | 143–144* |
| $SOCH_3$ | CN | $CH_3$ | $NO_2$ | 125–128 |
| $SOCH_3$ | CN | $CH_3$ | $CF_3$ | 164–166 |
| $SOCH_3$ | CN | $CH_3$ | $SOCH_3$ | 234–238 |
| Cl | CN | $CHCl_2$ | $SOCH_3$ | (gum) |

*Oxidation carried out with m-chloroperbenzoic acid in methylene dichloride solution.

EXAMPLE 8

A mixture of 4-nitro-3-trifluoromethyl-N-(2-hydroxy-2-p-methylthiophenylpropionyl)aniline (1.1 g.), glacial acetic acid (37 ml.) and hydrogen peroxide (2.8 ml., 100 vols.) was stirred at 70° C. for 5 hours, cooled, diluted with water (25 ml.) and extracted 3 times with ethyl acetate (25 ml. each time). The combined extracts were washed with saturated aqueous sodium chloride solution, dried over magnesium sulphate and evaporated to dryness under reduced pressure. The residue was crystallised from a mixture of ethyl acetate and toluene and there was thus obtained 4-nitro-3-trifluoromethyl-N-(2-hydroxy-2-p-methanesulphonylphenylpropionyl)aniline, m.p. 187°–189° C.

The process described above was repeated using the appropriate anilide bearing an alkylthio or arylthio substituent, and there were thus obtained the compounds described in the following table:

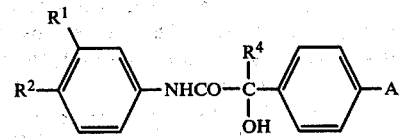

| $R^1$ | $R^2$ | $R^4$ | A | m.p. (°C.) |
|---|---|---|---|---|
| Cl | Cl | $CH_3$ | $SO_2CH_3$ | 212–215 |
| $CF_3$ | $NO_2$ | $CH_3$ | $SO_2C_6H_5$ | 79–82 |
| Cl | $SO_2CH_3$ | $CH_3$ | $NO_2$ | 200–201 |
| Cl | $SO_2CH_3$ | $CH_3$ | CN | 175–176 |
| Cl | $SO_2CH_3$ | $CH_3$ | $CF_3$ | 133–134 |
| H | $SO_2CH_3$ | $CH_3$ | $NO_2$ | 200–201 |
| H | $SO_2CF_3$ | $CH_3$ | $NO_2$ | 181–182 |
| $SO_2C_6H_5$ | $NO_2$ | $CH_3$ | $NO_2$ | (Not Crystalline) |
| Cl | Cl | $CHCl_2$ | $SO_2CH_3$ | 102–103 |
| Cl | Cl | $CHF_2$ | $SO_2CH_3$ | 168–170 |
| $SO_2CH_3$ | CN | $CH_3$ | $NO_2$ | 249–251* |

*Oxidation carried out at laboratory temperature.

EXAMPLE 9

Aqueous 2 N-sodium hydroxide solution (1.12 ml.) was added to a solution of methyl 2,3-epoxy-2-p-nitrophenylpropionate (0.5 g.) in a mixture of ethanol (15 ml.), tetrahydrofuran (3 ml.) and water (3 ml.) and the mixture was stirred at laboratory temperature for 1 hour and then evaporated to dryness under reduced pressure. The residue was suspended in toluene (20 ml.), oxalyl chloride (0.25 ml.) was added and the mixture was stirred at laboratory temperature for 2 hours. Pyridine (10 ml.) and 4-nitro-3-trifluoromethylaniline (0.462 g.) were added and the mixture was stirred at laboratory temperature for 2 hours and then evaporated to dryness under reduced pressure. The residue was partitioned between ethyl acetate and dilute aqueous hydrochloric acid and the ethyl acetate layer was washed successively with saturated aqueous sodium bicarbonate solution, water and saturated aqueous sodium chloride solution, dried over magnesium sulphate and evaporated to dryness under reduced pressure. The residual gum was dissolved in chloroform (50 ml.), the solution was saturated with hydrogen chloride and the mixture was stirred for 17 hours at laboratory temperature and then poured into water. The mixture was extracted three times with diethyl ether and the combined extracts were washed successively with saturated aqueous sodium bicarbonate solution, water and saturated aqueous sodium chloride solution, dried over magnesium sulphate and evaporated to dryness under reduced pressure. The residue was purified by chromatography on a silica gel column (20 g.) using a 2:3 v/v mixture of ethyl acetate and petroleum ether (b.p. 60°–80° C.) as eluant, and the product was crystallised from toluene. There was thus obtained 4-nitro-3-trifluoromethyl-N-(3-chloro-2-hydroxy-2-p-nitrophenylpropionyl)aniline, m.p. 154°–157° C.

The methyl 2,3-epoxy-2-p-nitrophenylpropionate used as starting material was obtained as follows:

Benzonitrile (1 ml.), potassium carbonate (0.2 g.) and 30% aqueous hydrogen peroxide solution (1.5 ml.) were added to a solution of methyl 2-p-nitrophenylprop-2-enoate (1.0 g.) in a mixture of methanol (15 ml.) and chloroform (15 ml.) and the mixture was stirred at laboratory temperature for 17 hours and then poured into water. The mixture was extracted three times with diethyl ether and the combined extracts were washed successively with water, aqueous ferrous sulphate solution and saturated aqueous sodium chloride solution, dried over magnesium sulphate and evaporated to dryness under reduced pressure. There was thus obtained as solid residue methyl 2,3-epoxy-2-p-nitrophenylpropionate which was used without further purification.

The process described above was repeated using the appropriate aniline in place of 4-nitro-3-trifluoromethylaniline, and there were thus obtained 3,4-dichloro-N-(3-chloro-2-hydroxy-2-nitrophenylpropionyl)aniline, m.p. 78°–82° C., and 3-chloro-4-cyano-N-(3-chloro-2-hydroxy-2-p-nitrophenylpropionyl)aniline, m.p. 186°–189° C.

EXAMPLE 10

Jones' reagent (a 25% w/w solution of chromium trioxide in sulphuric acid) was added to a solution of 3,4-dichloro-N-(2-p-formylphenyl-2-hydroxypropionyl)aniline (Example 3; 1.0 g.) in acetone (50 ml.) until a permanent yellow colour persisted, and the mixture was then filtered. The filtrate was evaporated to dryness under reduced pressure, the residue was dissolved in methanol (20 ml.), concentrated sulphuric acid (0.5 ml.) was added and the mixture was heated under reflux for 3 hours, cooled and poured into water. The mixture was extracted three times with diethyl ether and the combined extracts were washed successively with saturated aqueous sodium bicarbonate solution, water and saturated aqueous sodium chloride solution, dried over magnesium sulphate and evaporated to dryness under reduced pressure. The product was purified by chromatography on a silica gel column using a 1:1 v/v mixture of ethyl acetate and petroleum ether (b.p. 60°–80° C.). There was thus obtained 3,4-dichloro-N-(2-hydroxy-2-p-methoxycarbonylphenylpropionyl)aniline, m.p. 109° C.

The process described above was repeated using the appropriate p-formylphenyl compound, and there were thus obtained the compounds described in the following table:

| $R^1$ | $R^2$ | m.p. (°C.) |
|---|---|---|
| $CF_3$ | $NO_2$ | 87–88 |
| Cl | CN | 103–106 |

EXAMPLE 11

A solution of 4-nitro-3-trifluoromethylphenyl isocyanate (1.5 g.) in diethyl ether (30 ml.) was added dropwise to a stirred solution of methyl 2-hydroxy-2-p-nitrophenylpropionate (1.0 g.) and 1,3-diamino propane (0.1 g.) in diethyl ether (20 ml.), and the mixture was stirred at laboratory temperature for 65 hours and then filtered. The solid residue was crystallised from a mixture of toluene and petroleum ether (b.p. 60°–80° C.) and there was thus obtained 5-methyl-5-p-nitrophenyl-3-(4-nitro-3-trifluoromethylphenyl)oxazolidine-2,4-dione, m.p. 175°–177° C.

What we claim is:

1. An acylanilide of the formula:

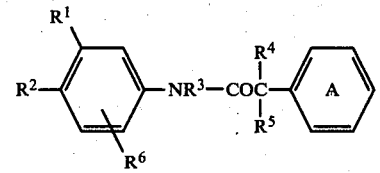

wherein $R^1$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl; wherein $R^2$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;

wherein $R^3$ is hydrogen or alkyl of up to 4 carbon atoms, or is joined to $R^5$ as stated below;
  wherein $R^4$ is alkyl of 2 to 4 carbon atoms, or has the formula $—CX^1X^2X^3$ wherein $X^1$, $X^2$ and $X^3$, which may be the same or different, each is hydrogen, fluorine or chlorine;
  wherein $R^5$ is hydrogen, hydroxy or alkoxy or acyloxy each of up to 15 carbon atoms, or is joined to $R^3$ to form an oxycarbonyl group such that together with the $$-\text{N}-\text{CO}-\overset{|}{\text{C}}-$$

part of the molecule it forms an oxazolidinedione group;
wherein $R^6$ is hydrogen or halogen;
and wherein the benzene ring A bears one, two or three substituents selected from halogen, nitro, carboxy, carbamoyl and cyano, and alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenylthio, phenylsulphinyl and phenylsulphonyl.

2. An acylanilide as claimed in claim 1 wherein
$R^1$ is cyano, carbamoyl, nitro, fluoro, chloro, bromo, iodo, hydrogen, methyl, ethyl, methoxy, ethoxy, formyl, acetyl, methylthio, ethylthio, methylsulphinyl, methylsulphonyl, trifluoromethyl, pentafluoroethyl, trifluoromethylthio, trifluoromethylsulphinyl, trifluoromethylsulphonyl, phenylthio, phenylsulphinyl or phenylsulphonyl;
wherein $R^2$ is cyano, carbamoyl, nitro, fluoro, chloro, bromo, iodo, formyl, acetyl, methylthio, ethylthio, methylsulphinyl, methylsulphonyl, trifluoromethyl, pentafluoroethyl, trifluoromethylthio, trifluoromethylsulphinyl, trifluoromethylsulphonyl, phenylthio, phenylsulphinyl or phenylsulphonyl;
wherein $R^3$ is hydrogen, methyl or ethyl, or is joined to $R^5$ as stated below;
wherein $R^4$ is methyl, ethyl, n-propyl, fluoromethyl, difluoromethyl, trifluoromethyl, chloromethyl, dichloromethyl or trichloromethyl;
wherein $R^5$ is hydrogen, hydroxy, methoxy, ethoxy, propyloxy, n-butyloxy, decyloxy, acetoxy, propionyloxy, decanoyloxy or dodecanoyloxy, or is joined to $R^3$ to form an oxycarbonyl group as stated in claim 1;
wherein $R^6$ is hydrogen or chloro;
and wherein the benzene ring A bears one or two substituents selected from fluoro, chloro, bromo, iodo, nitro, carboxy, carbamoyl, cyano, formyl, acetyl, methylthio, ethylthio, methylsulphinyl, methylsulphonyl, trifluoromethyl, pentafluoroethyl, trifluoromethylthio, trifluoromethylsulphinyl, trifluoromethylsulphonyl, methoxycarbonyl, ethoxycarbonyl, N-methylcarbamoyl, phenylthio, phenylsulphinyl and phenylsulphonyl.

3. An acylanilide as claimed in claim 1 wherein
$R^1$ is trifluoromethyl and $R^2$ is nitro or cyano; or
$R^1$ is chloro and $R^2$ is chloro, nitro, cyano, methylthio, methylsulphinyl or methylsulphonyl; or
$R^1$ is cyano and $R^2$ chloro; or
$R^1$ is nitro and $R^2$ is chloro or cyano; or
$R^1$ is methylthio and $R^2$ is cyano; or
$R^1$ is hydrogen and $R^2$ is methylthio;
wherein $R^3$ is hydrogen;
wherein $R^4$ is methyl;
wherein $R^5$ is hydroxy;
wherein $R^6$ is hydrogen;
and wherein the benzene ring A bears one or two substituents only, one of which is a nitro, fluoro, chloro, trifluoromethyl, cyano, methoxycarbonyl, methylthio, methylsulphinyl or methanesulphonyl substituent in the para-position and the other of which, if present, is chloro in the meta-position.

4. An acylanilide as claimed in claim 1 wherein $R^1$ and $R^2$, which may be the same or different, each is cyano, nitro, trifluoromethyl or chloro, $R^3$ and $R^6$ are both hydrogen, $R^4$ is methyl, $R^5$ is hydroxy and the ring A bears one substituent in the para-position which is a nitro, fluoro, trifluoromethyl, cyano, methoxycarbonyl, methylthio or methylsulphinyl substituent.

5. The compound 3,4-dichloro-N-(2-hydroxy-2-p-nitrophenylpropionyl)aniline;
4-nitro-3-trifluoromethyl-N-(2-hydroxy-2-p-nitrophenylpropionyl)aniline or
4-cyano-3-trifluoromethyl-N-(2-hydroxy-2-p-nitrophenylpropionyl)aniline.

6. The compound 3-chloro-4-nitro-N-(2-hydroxy-2-p-nitrophenylpropionyl)aniline;
3-chloro-4-methylsulphonyl-N-(2-hydroxy-2-p-nitrophenylpropionyl)aniline;
4-nitro-3-trifluoromethyl-N-(2-hydroxy-2-p-trifluoromethylphenylpropionyl)aniline;
3-chloro-4-nitro-N-(2-hydroxy-2-p-trifluoromethylphenylpropionyl)aniline;
4-nitro-3-trifluoromethyl-N-(2-p-cyanophenyl-2-hydroxypropionyl)aniline;
4-nitro-3-trifluoromethyl-N-(2-p-fluorophenyl-2-hydroxypropionyl)aniline;
4-nitro-3-trifluoromethyl-N-(2-hydroxy-2-p-methylsulphinylphenylpropionyl)aniline;
3,4-dichloro-N-(2-hydroxy-2-p-methylsulphinylphenylpropionyl)aniline; and
3,4-dichloro-N-(2-p-acetylphenyl-2-hydroxypropionyl)aniline.

7. A pharmaceutical or veterinary composition which comprises an effective anti-androgenic amount of an acylanilide, claimed in any of claims 1 to 6, in association with a pharmaceutically acceptable diluent or carrier.

8. A composition as claimed in claim 7 which additionally contains one or more drugs selected from antioestrogens, progestins, inhibitors or gonadotrophin secretion, cytotoxic agents, antibiotics and antiinflammatory agents.

9. A method of producing an antiandrogenic effect in a warm-blooded animal in need of such an effect which comprises administering to said animal an effective amount of an acylanilide claimed in any of claims 1 to 6.

* * * * *